(12) United States Patent
Chtourou

(10) Patent No.: US 11,553,712 B2
(45) Date of Patent: Jan. 17, 2023

(54) GLYCOLS AS PATHOGEN INACTIVATING AGENTS

(75) Inventor: Sami Chtourou, Elancourt (FR)

(73) Assignee: Laboratoire Français du Fractionnement et des Biotechnologies, Puteaux (FR)

( * ) Notice: Subject to any disclaimer, the term of this patent is extended or adjusted under 35 U.S.C. 154(b) by 200 days.

(21) Appl. No.: 13/994,207

(22) PCT Filed: Dec. 23, 2011

(86) PCT No.: PCT/IB2011/003271
§ 371 (c)(1),
(2), (4) Date: Jul. 23, 2013

(87) PCT Pub. No.: WO2012/090067
PCT Pub. Date: Jul. 5, 2012

(65) Prior Publication Data
US 2013/0324619 A1 Dec. 5, 2013

Related U.S. Application Data

(60) Provisional application No. 61/428,416, filed on Dec. 30, 2010.

(51) Int. Cl.
*A01N 31/02* (2006.01)
*A61L 2/00* (2006.01)
*A61L 2/18* (2006.01)

(52) U.S. Cl.
CPC ............ *A01N 31/02* (2013.01); *A61L 2/0088* (2013.01); *A61L 2/18* (2013.01); *A61L 2202/22* (2013.01)

(58) Field of Classification Search
CPC ......... A01N 31/02; A61L 2/0088; A61L 2/18; A61L 2202/22
See application file for complete search history.

(56) References Cited

U.S. PATENT DOCUMENTS

| | | | |
|---|---|---|---|
| 3,910,999 A * | 10/1975 | Moyer | B01J 19/0086 562/525 |
| 4,020,183 A | 4/1977 | Asculai et al. | |
| 4,299,828 A | 11/1981 | Wang et al. | |
| 4,420,398 A | 12/1983 | Castino | |
| 4,612,169 A | 9/1986 | Iwasaki et al. | |
| 4,764,369 A | 8/1988 | Neurath et al. | |
| 5,145,663 A | 9/1992 | Simmons | |
| 5,356,651 A | 10/1994 | Degen et al. | |
| 5,576,040 A | 11/1996 | Moller et al. | |
| 5,648,253 A | 7/1997 | Wei | |
| 5,756,687 A | 5/1998 | Denman et al. | |
| 5,827,690 A | 10/1998 | Meade et al. | |
| 5,843,705 A | 12/1998 | DiTullio et al. | |
| 5,849,992 A | 12/1998 | Meade et al. | |
| 6,210,736 B1 | 4/2001 | Echelard et al. | |
| 6,268,487 B1 | 7/2001 | Kutzko et al. | |
| 6,441,145 B1 | 8/2002 | DiTullio et al. | |
| 6,448,469 B1 | 9/2002 | Smith | |
| 6,472,584 B1 | 10/2002 | Smith | |
| 6,528,699 B1 | 3/2003 | Meade et al. | |
| 6,545,198 B1 | 4/2003 | Echelard et al. | |
| 6,548,653 B1 | 4/2003 | Young et al. | |
| 6,580,017 B1 | 6/2003 | Echelard et al. | |
| 6,593,463 B1 | 7/2003 | Chen et al. | |
| 6,727,405 B1 | 4/2004 | Gordon et al. | |
| 6,743,966 B2 | 6/2004 | Smith | |
| 7,019,193 B2 | 3/2006 | Ditullio et al. | |
| 7,026,154 B1 | 4/2006 | Gaillac et al. | |
| 7,045,676 B1 | 5/2006 | Gordon et al. | |
| 7,087,719 B2 | 8/2006 | Visuri et al. | |
| 7,101,971 B2 | 9/2006 | Meade et al. | |
| 7,354,594 B2 | 4/2008 | Chen et al. | |
| 7,501,553 B2 | 3/2009 | Chen et al. | |
| 7,531,632 B2 | 5/2009 | Perreault | |
| 7,550,263 B2 | 6/2009 | Meade et al. | |
| 7,632,980 B1 | 12/2009 | Chen et al. | |
| 7,651,686 B2 | 1/2010 | Chen et al. | |
| 7,928,064 B2 | 4/2011 | DiTullio et al. | |
| 7,939,317 B1 | 5/2011 | Gordon et al. | |
| 8,173,860 B2 | 5/2012 | Meade et al. | |
| 8,252,227 B2 | 8/2012 | Bardat | |
| 9,029,316 B2 | 5/2015 | Bardat et al. | |
| 9,102,762 B2 | 8/2015 | Christensen et al. | |
| 9,358,275 B2 | 6/2016 | Bardat et al. | |
| 9,511,087 B2 | 12/2016 | Frieling et al. | |
| 10,034,921 B2 | 7/2018 | Chen et al. | |

(Continued)

FOREIGN PATENT DOCUMENTS

CA 962514 A 2/1975
CN 101065118 A 10/2007
(Continued)

OTHER PUBLICATIONS

Dunham, W. B., and W. J. MacNeal. "Inactivation of Influenza Virus by Mild Antiseptics." Journal of Immunology 49.2 (1944): 123-8.*
Scientific Report of EFSA, Available data on notified biocides efficacy under field conditions (compared to sodium hydroxide and sodium carbonate), European Food Safety Authority, European Food Safety Authority (EFSA), EFSA Journal 2009; 7 (10):259 (Year: 2009).*

(Continued)

*Primary Examiner* — Kortney L. Klinkel
*Assistant Examiner* — Jason Deck
(74) *Attorney, Agent, or Firm* — Wolf, Greenfield & Sacks, P.C.

(57) ABSTRACT

The disclosure relates to uses, methods and compositions for the inactivation of pathogens in biological compositions, using a glycol as a pathogen inactivating agent.

20 Claims, 2 Drawing Sheets

(56) References Cited

U.S. PATENT DOCUMENTS

| | | |
|---|---|---|
| 10,174,110 B2 | 1/2019 | Meade et al. |
| 10,611,826 B2 | 4/2020 | Paolantonacci et al. |
| 2002/0131957 A1 | 9/2002 | Gavin et al. |
| 2002/0144299 A1 | 10/2002 | Chen et al. |
| 2002/0155998 A1 | 10/2002 | Young et al. |
| 2003/0005468 A1 | 1/2003 | Meade et al. |
| 2003/0033618 A1 | 2/2003 | Smith |
| 2003/0036637 A1 | 2/2003 | Fulton |
| 2003/0046716 A1 | 3/2003 | Echelard et al. |
| 2003/0096974 A1 | 5/2003 | Ditullio et al. |
| 2003/0177513 A1 | 9/2003 | Echelard et al. |
| 2003/0204860 A1 | 10/2003 | Melican et al. |
| 2003/0213003 A1 | 11/2003 | Meade et al. |
| 2004/0006776 A1 | 1/2004 | Meade et al. |
| 2004/0025193 A1 | 2/2004 | Echelard et al. |
| 2004/0092719 A1 | 5/2004 | Birck-Wilson et al. |
| 2004/0097710 A1 | 5/2004 | Visuri et al. |
| 2004/0098755 A1 | 5/2004 | Mulroy et al. |
| 2004/0102380 A1 | 5/2004 | Fulton et al. |
| 2004/0109847 A1 | 6/2004 | Chen et al. |
| 2004/0117863 A1 | 6/2004 | Edge et al. |
| 2004/0121303 A1 | 6/2004 | Gavin et al. |
| 2004/0133931 A1 | 7/2004 | Gavin et al. |
| 2004/0143857 A1 | 7/2004 | Young et al. |
| 2004/0148648 A1 | 7/2004 | Behboodi et al. |
| 2004/0167320 A1 | 8/2004 | Couto et al. |
| 2004/0192595 A1 | 9/2004 | Murakami et al. |
| 2004/0205832 A1 | 10/2004 | Meade et al. |
| 2004/0226052 A1 | 11/2004 | Meade et al. |
| 2004/0226053 A1 | 11/2004 | Meade et al. |
| 2005/0006307 A1 | 1/2005 | Jones et al. |
| 2005/0013811 A1 | 1/2005 | Chen et al. |
| 2005/0029195 A1 | 2/2005 | Gibson et al. |
| 2005/0060766 A1 | 3/2005 | Chen |
| 2005/0071890 A1 | 3/2005 | Chen et al. |
| 2005/0097625 A1 | 5/2005 | Meade et al. |
| 2005/0158832 A1 | 7/2005 | Young et al. |
| 2005/0160483 A1 | 7/2005 | Meade et al. |
| 2005/0169908 A1 | 8/2005 | Murakami et al. |
| 2005/0177882 A1 | 8/2005 | Gavin et al. |
| 2005/0181482 A1 | 8/2005 | Meade et al. |
| 2005/0186608 A1 | 8/2005 | Olsen |
| 2005/0192226 A1 | 9/2005 | Enkhbaatar et al. |
| 2005/0193431 A1 | 9/2005 | Echelard et al. |
| 2005/0197496 A1 | 9/2005 | Perreault |
| 2005/0208000 A1 | 9/2005 | Bernstein et al. |
| 2005/0235371 A1 | 10/2005 | Chen et al. |
| 2005/0245444 A1 | 11/2005 | Echelard et al. |
| 2005/0260672 A1 | 11/2005 | Couto et al. |
| 2006/0026695 A1 | 2/2006 | Edge et al. |
| 2006/0105347 A1 | 5/2006 | Meade et al. |
| 2006/0121004 A1 | 6/2006 | Echelard et al. |
| 2006/0123500 A1 | 6/2006 | Echelard et al. |
| 2006/0130159 A1 | 6/2006 | Masiello et al. |
| 2006/0168671 A1 | 7/2006 | Gavin et al. |
| 2006/0174359 A1 | 8/2006 | Melican et al. |
| 2006/0178309 A1 | 8/2006 | Visuri et al. |
| 2006/0179493 A1 | 8/2006 | Meade et al. |
| 2006/0179500 A1 | 8/2006 | Meade et al. |
| 2006/0182744 A1 | 8/2006 | Strome et al. |
| 2006/0191025 A1 | 8/2006 | Echelard et al. |
| 2006/0191029 A1 | 8/2006 | Gavin et al. |
| 2006/0286548 A1 | 12/2006 | Liposky et al. |
| 2007/0037192 A1 | 2/2007 | Ziomek et al. |
| 2007/0192878 A1 | 8/2007 | Perreault |
| 2008/0004212 A1 | 1/2008 | Echelard et al. |
| 2008/0019905 A9 | 1/2008 | Strome et al. |
| 2008/0063780 A1 | 3/2008 | Meade et al. |
| 2008/0118501 A1 | 5/2008 | Schindler et al. |
| 2008/0176786 A1 | 7/2008 | Ditullio et al. |
| 2009/0068193 A1 | 3/2009 | Chen et al. |
| 2009/0246194 A1 | 10/2009 | Meade et al. |
| 2009/0311239 A1 | 12/2009 | Chtourou et al. |
| 2010/0021612 A1 | 1/2010 | Meade et al. |
| 2010/0056757 A1 | 3/2010 | Perreault |
| 2011/0070167 A1 | 3/2011 | Enkhbaatar et al. |
| 2011/0082083 A1 | 4/2011 | Magneson et al. |
| 2011/0229460 A1 | 9/2011 | Meade |
| 2012/0058047 A9 | 3/2012 | Strome et al. |
| 2013/0149301 A1 | 6/2013 | Meade |
| 2013/0324619 A1 | 12/2013 | Chtourou |
| 2014/0046033 A1 | 2/2014 | Schindler et al. |
| 2014/0194360 A1 | 7/2014 | Frieling et al. |
| 2014/0206617 A1 | 7/2014 | Frieling et al. |
| 2014/0228301 A1 | 8/2014 | Meade et al. |
| 2014/0242182 A1 | 8/2014 | Evans et al. |
| 2014/0296490 A1 | 10/2014 | Faid et al. |
| 2015/0152162 A1 | 6/2015 | Boulange et al. |
| 2015/0175983 A1 | 6/2015 | Bataille et al. |
| 2015/0368334 A1 | 12/2015 | Meade et al. |
| 2015/0368357 A1 | 12/2015 | Meade et al. |
| 2015/0374801 A1 | 12/2015 | Chen et al. |
| 2016/0002330 A1 | 1/2016 | Meade |
| 2016/0039913 A1 | 2/2016 | Meade et al. |
| 2016/0089422 A1 | 3/2016 | Chtourou et al. |
| 2016/0129115 A1 | 5/2016 | Magneson et al. |
| 2016/0158676 A1 | 6/2016 | Hawkins et al. |
| 2016/0168229 A1 | 6/2016 | Paolantonacci et al. |
| 2016/0326547 A1 | 11/2016 | Meade et al. |
| 2017/0121402 A1 | 5/2017 | Chtourou |
| 2017/0129966 A1 | 5/2017 | Masiello |
| 2017/0190753 A1 | 7/2017 | Abache |
| 2018/0139938 A1 | 5/2018 | Chen |
| 2018/0169297 A1 | 6/2018 | Chtourou et al. |
| 2018/0355034 A1 | 12/2018 | Mondon et al. |
| 2019/0254276 A1 | 8/2019 | Chtourou |
| 2019/0309057 A1 | 10/2019 | Meade et al. |
| 2019/0309058 A1 | 10/2019 | Meade et al. |
| 2020/0255518 A1 | 8/2020 | Schindler et al. |
| 2020/0331994 A1 | 10/2020 | Chtourou et al. |
| 2021/0275668 A1 | 9/2021 | Plantier et al. |

FOREIGN PATENT DOCUMENTS

| | | |
|---|---|---|
| CN | 1829736 A | 9/2009 |
| EP | 0638242 A2 | 1/1995 |
| EP | 0 819 968 A1 | 1/1998 |
| EP | 0804074 B1 | 1/2005 |
| EP | 2350271 B1 | 1/2016 |
| JP | S46-6912 Y1 | 3/1971 |
| JP | S55-164627 A | 12/1980 |
| JP | S59-175879 A | 10/1984 |
| JP | H04-503067 A | 6/1992 |
| JP | H07-126109 A | 5/1995 |
| JP | H09-206362 A | 8/1997 |
| JP | H10-507367 A | 7/1998 |
| JP | 2008-531700 A | 8/2008 |
| JP | 2012-509081 A | 4/2012 |
| WO | WO 90/08559 A1 | 8/1990 |
| WO | WO 94/29334 A1 | 12/1994 |
| WO | WO 1995/002393 A1 | 1/1995 |
| WO | WO 9502393 A1 * | 1/1995 |
| WO | WO 96/14737 A1 | 5/1996 |
| WO | WO 99/64462 A1 | 12/1999 |
| WO | WO 1999/064441 | 12/1999 |
| WO | WO 2002/058747 A1 | 8/2002 |
| WO | WO 2004/011023 A1 | 2/2004 |
| WO | WO 2004/092360 A2 | 10/2004 |
| WO | WO 2006/093924 | 9/2006 |
| WO | WO 2009/110940 A2 | 9/2009 |
| WO | WO 2010/009388 A1 | 1/2010 |
| WO | WO 2010/059232 A1 | 5/2010 |
| WO | WO 2013/066251 A1 | 5/2013 |

OTHER PUBLICATIONS

Jack A. Ragheb, The Amphotropic and Ecotropic Murine Leukemia Virus Envelope . . . , Journal of Virology, Nov. 1995, p. 7205-7215 (Year: 1995).*

S. Davison, C. E. Benson, A. F. Ziegler, and R. J. Eckroade, Evaluation of Disinfectants with the Addition of Antifreezing Compounds Against Nonpathogenic H7N2 Avian Influenza Virus, Avian Diseases 43:533-537, 1999 (Year: 1999).*

(56) References Cited

OTHER PUBLICATIONS

The pressure washing forum (dated 2009, downloaded Aug. 22, 2019) (Year: 2009).*
O. H. Robertson, M.D.,The Bactericidal Action of Propylene Glycol Vapor on Microorganisms Suspended in Air. I, J Exp Med. Jun. 1, 1942; 75(6): 593-610 (Year: 1942).*
I. Olitzky, Antimicrobial Properties of a Propylene Glycol Based Topical Therapeutic Agent, Journal of Pharmaceutical Sciences, vol. 54, No. 5, May 1965, 787-788 (Year: 1965).*
Wikipedia page for Protein purification (Year: 2021).*
PCT/IB2011/003271, dated May 10, 2012, International Search Report and Written Opinion.
PCT/IB2011/003271, dated Jul. 11, 2013, International Preliminary Report on Patentability.
Burnouf et al., Nanofiltration of plasma-derived biopharmaceutical products. Haemophilia. Jan. 2003;9(1):24-37.
Hill et al., Guidelines on the selection and use of therapeutic products to treat haemophilia and other hereditary bleeding disorders. Haemophilia. Jan. 2003;9(1):1-23.
Mollerup et al., The Use of RP-HPLC for measuring activation and cleavage of rFVIIa during purification. Biotechnol Bioeng. Dec. 5, 1995;48(5):501-5.
Pedersen et al., Auto activation of human recombinant coagulation factor VII. Biochemistry. Nov. 28, 1989;28(24):9331-6.
Tomokiyo et al., Large-scale production and properties of human plasma-derived activated Factor VII concentrate. Vox Sang. Jan. 2003;84(1):54-64.
Aranha-Creado et al., Cumulative Viral Titer Reduction Demonstrated by Sequential Challenge of a Tangential Flow Membrane Filtration System and a Direct Flow Pleated Filter Cartridge. PDA J Pharm Sci Technol. Sep. 1997;51(5):208-212.
Bryant et al., Pathogen Inactivation: The Definitive Safeguard for the Blood Supply. Arch Pathol Lab Med. May 2007;131(5):719-33.
Chang, Transfusion therapy in critically ill children. Pediatr Neonatol. Apr. 2008;49(2):5-12. doi:10.1016/S1875-9572(08)60004-2.
Cohn et al., Preparation and Properties of Serum and Plasma Proteins. IV. A System for the Separation into Fractions of the Protein and Lipoprotein Components of Biological Tissues and Fluids 1a,b,c,d J Am Chem Soc. Mar. 1946;68:459-75.
Oncley et al., The Separation of the Antibodies, Isoagglutinins, Prothrombin, Plasminogen and β1-Lipoprotein into Subfractions of Human Plasma. J Am Chem Soc. Feb. 1949;71(2):541-50.
[No Author Listed] The pressure washing forum. Apr. 9, 2009. Retrieved from the internet on Aug. 22, 2019. 1 page.
Davison et al., Evaluation of disinfectants with the addition of antifreezing compounds against nonpathogenic H7N2 avian influenza virus. Avian Dis. Jul.-Sep. 1999;43(3):533-7.
Lorenz et al., Use-Dilution Test and Newcastle Disease Virus. Appl Microbiol. Jan. 1964;12:24-6.
Robertson et al., The bactericidal action of propylene glycol vapor on microorganisms suspended in air. I. J Exp Med. Jun. 1, 1942;75(6):593-610.
Extended European Search Report for Application No. EP 20173998.4 dated May 14, 2021.
Anthony et al., A strategy to estimate unknown viral diversity in mammals. mBio. Sep. 3, 2013;4(5):e00598-13. doi: 10.1128/mBio.00598-13.
EP 20173998.4, dated May 14, 2021, Extended European Search Report.

\* cited by examiner

Figure 2

GLYCOLS AS PATHOGEN INACTIVATING AGENTS

RELATED APPLICATIONS

This application is a national stage filing under 35 U.S.C. § 371 of international application PCT/IB2011/003271, filed Dec. 23, 2011, which claims the benefit under 35 U.S.C. § 119(e) of U.S. provisional application Ser. No. 61/428,416, filed Dec. 30, 2010, the disclosure of which is incorporated by reference herein in its entirety.

FIELD OF THE INVENTION

The present disclosure relates to uses, methods and compositions for the inactivation of pathogens in biological compositions.

BACKGROUND OF THE INVENTION

Use of biological compositions is important for developing and producing therapeutics (e.g., the production of recombinant proteins). Biological compositions, such as blood compositions, save many lives by blood transfusion for instance, for patients having a blood disease, a haemorrhage, or undergoing a surgical procedure. However, the presence of pathogens in biological compositions presents a significant health risk.

Methods to inactivate pathogens in biological compositions have been developed. Classical pathogen inactivation methods include approaches based on heat treatment, solvent and/or detergent treatment, gamma irradiation, UV treatment, and leukodepletion. However, the efficiency and effectiveness of said methods varies because of the different sensitivities of pathogens and incompatibility of some methods with specific biological compositions.

There is a need for new pathogen inactivation methods and agents.

SUMMARY OF THE INVENTION

The present disclosure relates to uses, methods, agents and compositions for the inactivation of pathogens in biological compositions.

In one aspect the disclosure relates to the use of a glycol as a pathogen inactivating agent. In some embodiments the glycol is propylene glycol.

In one aspect the disclosure relates to methods for inactivating a pathogen in a biological composition, said method comprising contacting said biological composition with a glycol. In some embodiments for inactivating a pathogen in a biological composition, the glycol is propylene glycol. In some embodiments for inactivating a pathogen in a biological composition, said biological composition is a blood composition or a milk composition. In some embodiments for inactivating a pathogen in a biological composition, said pathogen is selected from the group consisting of viruses, bacteria, fungi, protozoa, parasites, and prions. In some embodiments said virus is selected from the group consisting of X-MuLV, PRV, BVDV and TGEV virus. In some embodiments for inactivating a pathogen in a biological composition, said method results in a pathogen elimination equal or greater than 4 $Log_{10}$TCID (Tissue Culture Infective Dose) according to the methods of Kärber and/or Spearman-Kärber. In some embodiments for inactivating a pathogen in a biological composition, the concentration of glycol after the contacting step is between 40 and 50% (w/w) of the biological composition. In some embodiments for inactivating a pathogen in a biological composition, the concentration of glycol after the contacting step is between 40 and 50% (v/v) of the biological composition. In some embodiments for inactivating a pathogen in a biological composition, said method is performed at a temperature between 15 and 25° C. In some embodiments for inactivating a pathogen in a biological composition, said method is performed at a pH between 7.0 and 8.0.

In one aspect the disclosure relates to a biological composition comprising a glycol, wherein said biological composition is obtained by any of the methods described herein In some embodiments said glycol is at a concentration between 40 and 50%. In some embodiments said glycol is propylene glycol. In some embodiments the biological composition is a milk composition or a blood composition.

BRIEF DESCRIPTION OF THE DRAWINGS

The drawings form part of the present specification and are included to further demonstrate certain aspects of the present disclosure. The disclosure may be better understood by reference to one or more of these drawings in combination with the detailed description of specific embodiments presented herein. The figures are illustrative only and are not required for enablement of the disclosure.

FIG. 2 shows BVDV inactivation in an affinity chromatography eluate containing 45% propylene glycol.

DETAILED DESCRIPTION OF THE INVENTION

Figure 1:
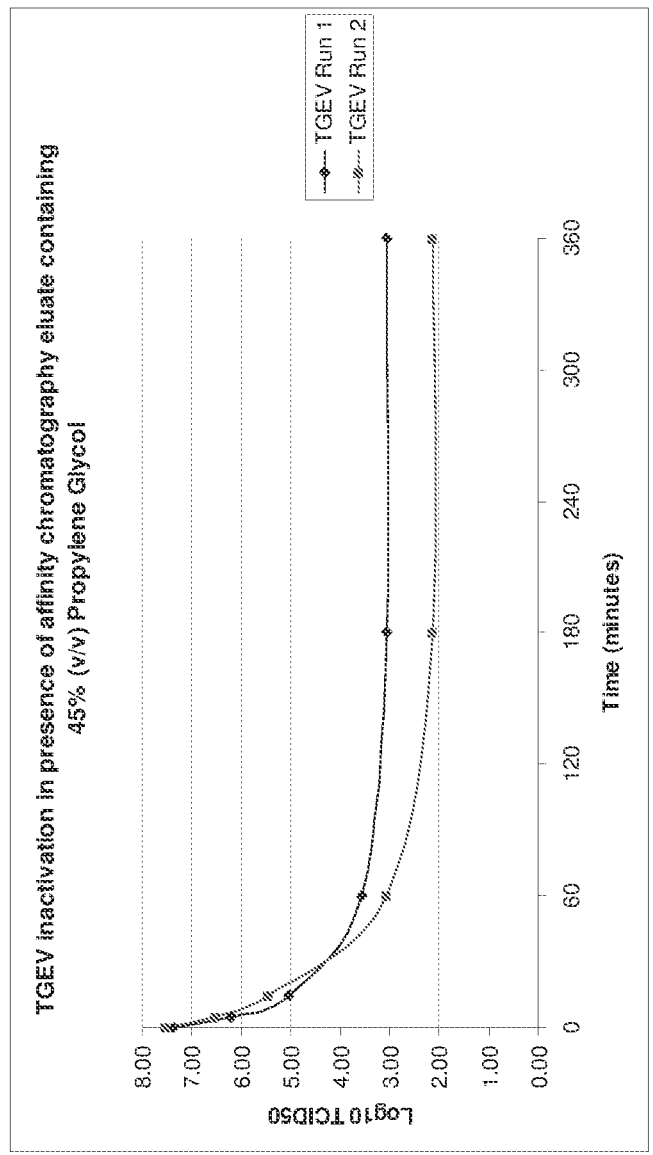
FIG. 1 shows TEGV inactivation in an affinity chromatography eluate containing 45% of propylene glycol.

In one aspect the disclosure relates to the use of a glycol as a pathogen inactivating agent. In one aspect the disclosure relates to methods for inactivating pathogens in a biological composition, said method comprising contacting said biological composition with a glycol. In one aspect the disclosure relates to a biological composition comprising glycol. In some embodiments said biological composition comprising glycol is obtained by any of the methods described herein.

In some embodiments of the uses, methods and compositions described herein, the glycol is vicinal glycol. In some embodiments the vicinal glycol is propylene glycol or ethylene glycol.

The term "glycol" (or "diol") refers to a chemical compound containing two hydroxyl groups (—OH). The term "vicinal glycol" refers to a glycol with two hydroxyl groups attached to adjacent atoms (e.g., in vicinal position).

In some embodiments the glycol used in the methods and compositions described herein is a vicinal glycol comprising between two and six carbons and having a chemical formula $R_1R_2$—(C—OH)$_2$—$R_3R_4$, wherein $R_1$, $R_2$, $R_3$ and $R_4$ may be identical or different and are each either a hydrogen atom or an alkyl group, wherein the combination of $R_1$, $R_2$, $R_3$ and $R_4$ contains at most two carbon atoms. Examples of vicinal glycols are propylene glycol, ethylene glycol, 1,2-butanediol and 1,2-pentanediol.

In some embodiments of the uses, methods and compositions described herein, the glycol is propylene glycol or ethylene glycol.

The term "propylene glycol", also called "1,2-dihydroxypropane" or "methyl glycol", refers to propane-1,2-diol and has the structural formula (I) represented below.

The term "ethylene glycol", also called "1,2-dihydroxy-ethane", refers to ethane-1,2-diol and has the structural formula (II) represented below.

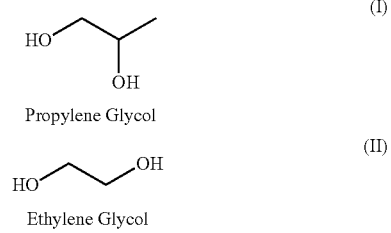

In some embodiments of the uses, methods and compositions described herein, the glycol is a geminal glycol. Geminal glycols have two hydroxyl groups attached to the same carbon atom and include 1,2-methane diol, 1,2-ethane diol and 1,2-propanediol. In some embodiments of the uses, methods and compositions described herein, the glycol is a diol wherein the hydroxyl groups are not on the same or adjacent carbon atoms. Examples of such glycols are 1,3-butanediols, 1,4-pentanediols, and 1,3-benzenediol.

In one aspect the disclosure relates to pathogen inactivating agents, compositions that comprise such agents and uses thereof.

The term "pathogen" refers to any biological agent (e.g., any nucleic acid containing agent or proteinaceous infectious particle such as a prion) that can cause disease in a mammal, such as a human. The term pathogen includes unicellular and multicellular microorganisms, with DNA or RNA as genetic material, in single-stranded or double-stranded form. The term particularly includes viruses, bacteria, fungi, protozoa and prions. Examples of bacteria include, but are not limited to, *Streptococcus, Escherichia* and *Bacillus* species; examples of viruses include, but are not limited to, the Human Immunodeficiency Virus (HIV) and other retroviruses, the herpesviruses, the paramyxoviruses, the poxviruses, the togaviruses, the cytomegaloviruses and the hepatitis viruses (HAV, HBV, HCV); examples of parasites include, but are not limited to, malaria parasites (*Plasmodium* species) and trypanosomal parasites.

In some embodiments of the disclosure, said pathogen to be inactivated is selected from the group consisting, of viruses, bacteria, fungi, protozoa, parasites and prions.

In some embodiments said pathogen is a virus.

In some embodiments said virus is an enveloped virus or a non-enveloped virus.

Enveloped viruses are viruses that have a host-cell-like "envelope" and include for example, but are not limited to, mammalian or avian Leukemia viruses, Herpes viruses, Pox viruses, Hepadnaviruses, Flaviviruses, Togaviruses, Coronaviruses, Hepatitis viruses, Retroviruses, Orthomyxoviruses, Paramyxoviruses, Rhadoviruses, Bunyaviruses, Filoviruses and Reoviruses. Non-enveloped viruses, also called naked viruses, are well known in the art and include, but are not limited to, adenoviruses, norovirus, rotavirus and human pappillomavirus.

In a some embodiments the virus is X-MuLV, PRV, TGEV or BVDV. The term "X-MuLV" for "Xenotropic murine leukemia virus-related virus" refers to a gammaretrovirus. The term "PRV" refers to a pseudorabies virus. The term "TGEV" for "Transmissible Gastroenteritis Coronavirus" refers to a species of animal virus belonging to the family of Coronaviruses. The term "BVDV" for "Bovine viral diarrhea virus" is a pestivirus from the family of flaviviruses.

In one aspect the disclosure relates to methods for inactivating pathogens in a biological composition, said method comprising contacting said biological composition with a glycol.

As used herein, the term "contacting" refers to a process of bringing into contact at least two distinct compositions or components such that they can interact.

The term "biological composition" refers to a composition (or a material) originating from a biological organism, including mammals. Examples of biological compositions include, but are not limited to, blood compositions, milk (such as milk from transgenic mammals), clinical samples such as urine, sweat, sputum, feces and spinal fluid, cellular and tissue extracts, cell culture medium, etc. As used herein, biological compositions also include synthetic compositions that can function as biological compositions, such as blood substitutes, and compositions that have undergone one or more purification or separation steps.

According to the disclosure a blood composition includes, but is not limited to, whole blood and blood products. The term "blood product" refers to one or more components that may be separated from whole blood, and encompasses cellular blood component (such as erythrocytes or red blood cells, platelets, leukocytes and concentrates thereof), blood proteins (such as blood clotting factors, enzymes, albumin, plasminogen, immunoglobulins) and blood fluid components (such as plasma, fractions of blood plasma and serum). In some embodiments the blood composition is leukodepleted (e.g., depleted in leukocytes).

In some embodiments the blood composition to be treated is selected from the group consisting of whole blood, erythrocytes concentrates, platelets concentrates, plasma and fractions of blood plasma.

In some embodiments the biological composition is a milk composition. In some embodiments the milk composition to be treated is derived from milk of a transgenic animal that produces a protein of interest secreted in said milk.

In some embodiments the method is performed on an eluate in a process of purification, such as by affinity chromatography, of a biological composition, such as a milk composition.

The terms "pathogen inactivation" or "inactivating pathogens", as used herein, refer to the suppression or inhibition of the replication (or reproduction) of said pathogens, and/or their destruction or elimination. Typically, a pathogen inactivating agent severely or at least substantially hampers the ability of the pathogen to replicate or reproduce under appropriate conditions.

Methods for determining if a particular method results in the suppression or inhibition of replication of pathogens are well known in the art. Typically such methods include the steps of determining the number of (active) pathogens prior to treatment with a pathogen inactivating agent and determining the number of (active) pathogens after treatment. The particular method for determining the number of active pathogens will depend on the nature of the pathogen and includes colony forming assays (for determining the number of active bacteria) and infective assays (for determining the number of "active" viruses). One measure of the number of active viruses is the Tissues Culture Effective Dose (TCID), which can be determined for instance by the Kärber and/or Spearman-Kärber methods. (See e.g., Karber, G. (1931). Arch. J. Exper. Path. u. pharmakol., 162, 480; Spearman (1908). Brit. J. Psychol., 2:227-242)

In some embodiments the methods of the disclosure result in pathogen elimination higher or equal to 4 $Log_{10}TCID$. The pathogen elimination may be calculated according to the methods of Kärber and/or Spearman-Kärber as explained in the examples.

In some embodiments the biological composition, after the contacting step, will contain an amount of glycol sufficient to inactivate, eliminate or lower the amount of pathogen, for example, below a desired level. In some embodiments the glycol concentration in the biological composition after the contacting step is between 10% and 75% (w/w), between 15% and 70% (w/w), between 20% and 65% (w/w), between 25% and 60% (w/w), between 30% and 60% (w/w), between 35% and 55% (w/w), or between 40% and 50% (w/w) of the composition. In some embodiments the glycol concentration in the biological composition after the contacting step is between 10% and 75% (v/v), between 15% and 70% (v/v), between 20% and 65% (v/v), between 25% and 60% (v/v), between 30% and 60% (v/v), between 35% and 55% (v/v), or between 40% and 50% (v/v) of the composition.

While not required, generally, it is expected that the pathogen inactivation increases with the length of exposure of the biological composition comprising the pathogen to the glycol. In some embodiments the biological composition is contacted with the glycol for a duration that permits pathogen elimination greater than or equal to 4 Log TCID (Tissue Culture Infective Dose)

In some embodiments the biological composition is contacted with the glycol for at least 10 minutes, at least 20 minutes, at least 30 minutes, at least 40 minutes, at least 50 minutes, at least 60 minutes, at least 70 minutes, at least 80 minutes, at least 90 minutes, at least 1200 minutes, at least 150 minutes, at least 180 minutes, at least 210 minutes, at least 240 minutes, at least 300 minutes, at least 360 minutes, at least 2500 minutes, at least 1000 minutes, or more. In some embodiments the biological composition is contacted with the glycol for a duration between 15 and 360 minutes, between 60 and 240 minutes, or between 90 and 180 minutes. In some embodiments the glycol is removed from the biological composition after a specific amount of pathogen inactivation has been achieved. In some embodiments the glycol remains present in the biological composition after the inactivation of the pathogen.

In some embodiments of the methods described herein are performed at a temperature between 10 and 30° C., between 12 and 28° C., or between 15 and 25° C.

In some embodiments the methods described herein are performed at a pH between 4 and 11, between 5 and 10, between 6 and 9, between 6.5 and 8.5, or between 7 and 8. In some embodiments the methods described herein are performed at a pH of around 7.5. In some embodiments the methods described herein are performed at a pH of 7.5. A person of ordinary skill in the art can rely on the literature to determine which pH range is acceptable for a particular biological composition.

In some embodiments the methods comprise a further step of viral elimination such as nanofiltration.

In some embodiments the methods are performed during an elution phase in a process of purification, such as affinity chromatography, of a biological composition. In some embodiments the glycol is added to an affinity elution buffer. In some embodiments an affinity elution buffer comprises 50 mM tris, 45% (w/w/) propylene glycol and 1.5M NaCl and has a pH of 7.5. In some embodiments an affinity elution buffer comprises 50 mM tris, 45% (v/v/) propylene glycol and 1.5M NaCl and has a pH of 7.5.

In some embodiments the methods described herein do not comprise a step of contacting the biological composition with cruciferous oil or with arginine in a significant amount.

A significant amount of arginine, as used herein, corresponds to an arginine concentration of at least 0.2M, at least 0.01M, or at least 0.001M, after the contacting step.

A significant amount of cruciferous oil, as used herein, corresponds to a concentration of at least 0.1% of said cruciferous oil, at least 0.01%, or at least 0:001%, after the contacting step.

In one aspect the disclosure relates to a biological composition comprising glycol for inactivating pathogens, wherein said biological composition is obtained by contacting a biological composition with a glycol, such as by any of the methods described herein.

In some embodiments said glycol is propylene glycol or ethylene glycol.

In some embodiments the glycol concentration in the biological composition is between 10% and 75% (w/w), between 15% and 70% (w/w), between 20% and 65% (w/w), between 25% and 60% (w/w), between 30% and 60% (w/w), between 35% and 55% (w/w), or between 40% and 50% (w/w) of the composition. In some embodiments the glycol concentration in the biological composition is between 10% and 75% (v/v), between 15% and 70% (v/v), between 20% and 65% (v/v), between 25% and 60% (v/v), between 30% and 60% (v/v), between 35% and 55% (v/v), or between 40% and 50% (v/v) of the composition.

In some embodiments the biological composition also comprises a detergent such as TWEEN 20 or TWEEN 80. In some embodiments the biological composition also comprises a solvent such as TNBP (Tri-N-butyl Phosphate). In some embodiments the biological composition comprised a detergent prior to contacting with glycol. In some embodiments the biological composition is contacted with a detergent prior to contacting with glycol. In some embodiments the biological composition is contacted with a detergent simultaneously with contacting with glycol. In some embodiments the biological composition is contacted with a detergent after contacting with glycol.

In some embodiments the biological composition does not comprise arginine in a significant amount.

In some embodiments the biological composition does not comprise cruciferous oil in a significant amount.

In some embodiments the biological composition does not comprise either arginine or cruciferous oil in a significant amount.

EXAMPLES

The following examples describe some embodiments of making and practicing the methods and compositions of the disclosure. However, it should be understood that the examples are for illustrative purposes only and are not meant to limit the scope of the disclosure. The entire contents of all of the references (including literature references, issued patents, published patent applications, and co-pending patent applications) cited throughout this application are hereby expressly incorporated by reference.

Material and Methods

The inactivation of two enveloped viruses (TGEV and BVDV) by propylene glycol (PG) present at 45% (v/v) in an affinity chromatography eluate was evaluated. The eluate was generated during the production of a transgenic protein of interest (in a milk composition derived from a transgenic animal producing said protein, which is secreted in its milk).

Cytotoxicity, Viral Interference and Quenching.

The cytotoxicity, viral interference and quenching parameters of the starting material (the eluate) were determined prior to the incubation assay in presence of PG. The assays to determine the cytotoxicity, viral interference and quenching were done on the eluate sample of an affinity chromatography.

Cytotoxicity.

The cytotoxicity parameters of the starting material were evaluated using the conditions in Table I:

TABLE I samples for evaluation of the cytotoxicity and tested dilutions.

| Sample to inoculate | Dilution range | Cells and associated virus | Observation post-inoculation |
|---|---|---|---|
| Starting matrix (eluate) | Undiluted to 1/243 (range of 3) | ST (swine testis) TGEV | Day +3/6 |
| | | MDBK (Madin-DarbyBovine Kidney) BVDV | Day +3/6 |

The non cytotoxic concentration of the sample matrix is defined as the first dilution of the sample matrix that does not involve any destruction of the cell coat of cells incubated into the matrix.

The cytotoxicity parameters obtained at Day +3 in this assay were used to determine the viral interference conditions and were confirmed at Day +6.

Viral Interference Control and Sample Quenching.

The viral interference and the sample quenching parameters were determined simultaneously.

The viral interference parameters of a sample for the titration system were evaluated. The assay consists of a dilution titration of the viruses BVDV and TGEC in a sample matrix (first dilution point: non-cytotoxic matrix, as determined above) compared with a titration in a culture medium. Before determining the appropriate dilutions of the viruses, a 30 minutes incubation period at 4° C. was performed in order to mimic the assay environment, as the actual assay has latency times of 15-30 minutes prior to the titration of fractions at T0, T5 and T15.

The potential interference of the matrix with both titration systems (ST and MDBK cells) was evaluated according to the operating conditions shown in Table II.

TABLE II operating conditions of interference.

| Cells | Virus | Diluent | Dilution range of the diluent | Post-inoculation observation |
|---|---|---|---|---|
| MDBK | BVDV | Starting matrix (eluate) at non toxic concentration | 1st timepoint: non-cytotoxic matrix + 3 other dilution points (growing) at a range of 3. | D +6 |
| | | Culture medium | undiluted | D +6 |
| ST | TGEV | Starting matrix (eluate) at non toxic concentration | 1st timepoint: non-cytotoxic matrix + 3 other dilution points (growing) at a range of 3. | D +6 |
| | | Culture medium | undiluted | D +6 |

The viral interference/quenching by the matrix was determined to be significant if a difference >1.0 $\log_{10}$ $TCID_{50}$/mL was observed between the titration in sample matrix (the eluate) and the titration in culture medium.

Process

Operating Conditions.

The kinetics of the inactivation of the enveloped viruses (TGEV and BVDV) by the propylene glycol (PG) was evaluated by contacting the viruses for six hours at 20° C. (±5° C.) with the eluate of the affinity chromatography containing 45% (v/v) PG as obtained during the purification process of the transgenic protein. The virus was added to the sample at a concentration of 5% (v/v). For each virus, the assay was performed in duplicate.

Material.

The starting material was an affinity chromatography eluate. The starting material was spiked with virus at 5% (v/v).

The conditions of the viral suspensions of TGEV and BVDV used in this assay are described in Table III (TEGV) and Table IV (BVDV).

TABLE III

| TGEV spikes. | |
|---|---|
| Virus used | TEGV (clarified supernatant) |
| Medium | Cell Culture medium ST |
| Aliquots | 5 × 5 mL, 4 × 1 mL, 81 × 80 μL |
| Titer | 8.53$\log_{10}$ $TCID_{50}$/mL ± 0.5$\log_{10}$ |
| Storage | <−65° C. |

TABLE IV

| BVDV spikes. | |
|---|---|
| Virus used | BVDV (clarified supernatant) |
| Medium | Cell Culture medium MDBK |
| Aliquots | 10 × 3 mL, 1 × 11 mL, 81 × 0.2 mL |
| Titer | 6.08$\log_{10}$ $TCID_{50}$/mL ± 0.5$\log_{10}$ |
| Storage | <−65° C. |

Respective cell Culture media (for ST and MDBK cells) were used during the neutralization step. This neutralization was performed at concentrations determined in the assays on the cytotoxicity, the viral interference and the matrix quenching.

Assay.

A beaker was placed in a heating device at 20° C.±5° C. The beaker was placed on a magnetic stirrer and maintained at 20° C.±5° C. before treatment.

For each assay, an aliquot of starting material (20 mL) was thawed in a water bath at 20° C.±5° C. After thawing, the temperature was checked.

Each aliquot (≥1 mL) of viral suspension was thawed at ambient temperature. An aliquot of about 0.1 mL was stored at a temperature lower than −65° C. The viral suspension was used to create a sample of the starting material containing 5% of virus.

The treatment consist of spiking 1 mL (5%) of viral suspension in 19 mL of matrix containing 45% of PG (obtained from the eluate of the affinity chromatography).

After a rapid homogenization and a check of the temperature of the mixture, a sample aliquot (1 mL) was taken and quenched with culture medium (ST cell culture medium or MDBK cell culture medium, depending on the cell line used). The added volume of cell culture medium depended on the data obtained in the cytotoxicity, interference and viral quenching study. This sample constituted the "T0".

The virus-spiked material (containing PG at 45% (v/v) was incubated for six hours at 20° C.±5° C. in the same manner as for the "T0" sample, sample aliquots of 1 mL were taken (and immediately diluted) after incubation periods of: T=5 min, T=15 min, T=60 min, T=180 min, T=360 min.

The samples collected during the different incubation assays of the eluate matrix "FVII Select" (that contain PG at 45%) are summarized in the Table V.

TABLE V

Designation of the collected samples during assays.

| Fractions | TGEV treatment | | BVDV Treatment | |
| --- | --- | --- | --- | --- |
| | Assay A | Assay B | Assay A | Assay B |
| Spike | Spike A TEGV | Spike B TEGV | Spike A BVDV | Spike B BVDV |
| Incubation T = 0 min | T0A TGEV | T0B TGEV | T0A BVDV | T0B BVDV |
| Incub. T = 5 min | T5A TGEV | T5B TGEV | T5A BVDV | T5B BVDV |
| Incub. T = 15 min | T15A TGEV | T15B TGEV | T15A BVDV | T15B BVDV |
| Incub. T = 60 min | T60A TGEV | T60B TGEV | T60A BVDV | T60B BVDV |
| Incub. T = 180 min | T180A TGEV | T180B TGEV | T180A BVDV | T180B BVDV |
| Incub. T = 360 min | T360A TGEV | T360B TGEV | T360A BVDV | T360B BVDV |

The samples, after titration, were stored at a temperature below −65° C. In addition, controls were generated with low, average and high viral load, by spiking of the matrix diluted in a non-cytotoxic and non-interfering concentration with the TGEV and BVDV viruses.

The incubation assays of the matrix containing 45% PG were considered successful if the following conditions were satisfied:
 a temperature of 20° C.±5° C. and a incubation period of 6 hours,
 taking of the sample aliquots as planned.

Titration of the Samples of Process.

The titration of the samples generated during the above-described assays was done on the same day.

Titration Protocol.

The titration of viruses of the samples shown in Table III was performed according to the study L-50 for TGEV and L-319 for BVDV.

The titration was done in three steps: seeding of the 96-wells plates, infection of said plates in standard titration or LVP (Large Volume Plating) and determination of the titer.

Seeding conditions of the 96-wells plates for the titration of each of the viruses are described in Table VI.

TABLE VI seeding conditions of the 96-wells plates for the titration of BVDV and TGEV.

| Seeding features | BVDV | TGEV |
| --- | --- | --- |
| Support | 96-wells plates | |
| Cells | MDBK | ST |
| Number of cells/well | 1000 | 3000 |
| Cell volume/well | 100 µL | |
| Culture medium | DMEM + 2% HS + P/S + NEAA | OptiMEM + 5% SVF + P/S + NEAA + NaPyruvate |
| Incubation period of plates | 18 hours ± 6 hours (overnight) | |

For each virus:
 samples obtained by the first run (Table V) were first titrated by the standard protocol,
 fractions obtained by the first run for which no virus was detected with the standard protocol were analyzed in Large Volume Plating (LPV) similar to samples obtained by the second run,
 if no virus was detected in the standard protocol, the first sample and the last sample (sample collected after 6 hours of incubation) were minimally titrated using LVP.

The titrations were performed immediately after the treatment assays; without freezing the samples.

Standard Titration.

The culture supernatant was removed and replaced by 20 µL of the sample to be titrated.

After a one-hour incubation at 37° C., 130 µL of culture medium was added to each well. Viral propagation resulted in a total or partial destruction of the cell coat.

For each dilution, 12 infection replicates were performed in order to permit a statistic analysis according to the Kärber and/or Spearman-Kärber methods, (See e.g., Chapter 5 of "Virology Labfax", Bios Publishers (plus Academic Press (US), or Blackwell non-US, 1993; Karber, G. (1931). Arch. J. Exper. Path. u. pharmakol., 162, 480; Spearman (1908). Brit. J. Psychol., 2:227-242).

LVP Titration.

The viral titration method "Large Volume Plating" in "n" replicates allows for an increase in tested sample volume and thus an increase in the detection limit. The protocol is identical to the standard titration, except that the analysis was done using only one sample dilution, placed in all the wells of one or more 96-wells plate(s). The statistic analysis was done according to the method of Spearman-Kärber.

Controls.

In parallel with the sample titration, the following controls were performed:

a negative control was used for each titration series. This control consists of a titration of the culture medium (used in the titration series) with the conditions used in the sample titration.

A positive control was also used for each titration series. In this study, BVDB and TGEV were used as a positive control. The titer of these positive controls was 6.08 $\log_{10}$ TCID$_{50}$/mL and 6.41 $\log_{10}$ TCID$_{50}$/mL±0.5 $\log_{10}$ TCID$_{50}$/mL.

Validity of a Titration Assay.

A titration assay was considered valid if:

No destruction of the cell coat was observed with the negative control.

The sample titration shows a rate of positive wells between 0 and 100% for at least three successive dilutions.

For at least the last dilution of the sample, a positive well rate equal to 0% is recognized.

Calculation of Titers, Charges and Reduction Factor.

After an incubation period of six days (for each of the viruses), for each well of each of the dilutions, the number of cells that had a total or partial destruction of the cell coat were quantified (with a microscope at size ×40 and/or ×100). The virus titer in each well was determined according to the Kärber formula, expressed in TCID$_{50}$/mL (in $\log_{10}$).

The titer of viral suspension was calculated according to the Karber method. The titration of a virus was given with an uncertainty of ±0.5 $\log_{10}$ TCID$_{50}$/mL and was calculated with the formula:

$$IC_{(\alpha=5\%)} = 1.96 \times 2\sqrt{\frac{\Sigma(p_i x q_i)}{(n-1)}}$$

wherein: $p_i$ is the rate of positive wells at dilution i.
$q_i$ is the rate of negative wells at dilution i.

However, if the virus was only observed at the first tested dilution of the sample, and its infection rate was lower than 100%, the logarithmic concentration of virus in TCID$_{50}$/mL was calculated according to the formula of the method of Spearman Kärber:

$$\mathrm{Log}_{10}\ C = \mathrm{log}10\left[\frac{\log_e\left(\frac{n}{n-r}\right)}{v.\log_e(2)}\right]$$

wherein
C is the virus concentration in TCID$_{50}$/mL,
v is the inoculum volume per well
n is the number of inoculated wells for each dilution
r is the number or infected wells.

With the titers and viral loads expressed here in decimal value, the total viral load in a sample was calculated with the titer and the sample volume according to this formula:

Total viral load=titer×sample volume(mL).

The reduction factor (RF) was calculated compared to the viral load in the <<T0>> sample.

RF=(total viral load in "T0")/(total viral load in sample taken at a later time).

Results

TGEV Study on the Affinity Chromatography Eluate (in Presence of 45% PG).

The results are described in Table VIII and illustrated in FIG. 1.

TABLE VIII

| Timepoint Sample | Volume (ml) | Titre ($\log_{10}$TCID$_{50}$/ml) | Correction (cytotoxicity) | Log10TICD50 | Reduction Factor (log) | Clearance Factor (log) | Titration |
|---|---|---|---|---|---|---|---|
| TGEV - Run 1 | | | | | | | |
| Spike | 1 | 7.45 | N/A | 7.45 | NA | NA | Standard |
| T = 0 Load Sample | 20 | 5.12 | 9 | 7.38 | NA | 0.07 | Standard |
| T = 5 | 20 | 3.95 | 9 | 6.21 | 1.17 | 1.24 | Standard |
| T = 15 | 20 | 2.78 | 9 | 5.04 | 2.34 | 2.41 | Standard |
| T = 60 | 20 | 1.32 | 9 | 3.58 | 3.8 | 3.87 | Standard |
| T = 180 | 20 | 0.8 | 9 | 3.06 | 4.32 | 4.39 | Standard |
| T = 360 | 20 | <0.8 | 9 | <3.06 | >4.32 | >4.39 | Standard |
| TGEV - Run 2 | | | | | | | |
| Spike | 1 | 7.62 | N/A | 7.62 | NA | NA | Standard |
| T = 0 Load Sample | 20 | 5.28 | 9 | 7.54 | NA | 0.08 | Standard |
| T = 5 | 20 | 4.28 | 9 | 6.54 | 1 | 1.08 | Standard |
| T = 15 | 20 | 3.2 | 9 | 5.46 | 2.08 | 2.16 | Standard |
| T = 60 | 20 | 0.8 | 9 | 3.06 | 4.48 | 4.56 | Standard |
| T = 180 | 20 | −0.12 | 9 | 2.14 | 5.4 | 5.48 | 1LVP (96 wells) |
| T = 360 | 20 | <−0.12 | 9 | <2.14 | >5.40 | >5.48 | 1 LVP (96 wells) |

BVDV Study on the Affinity Chromatography Eluate (in Presence of 45% PG).

Figure 2:
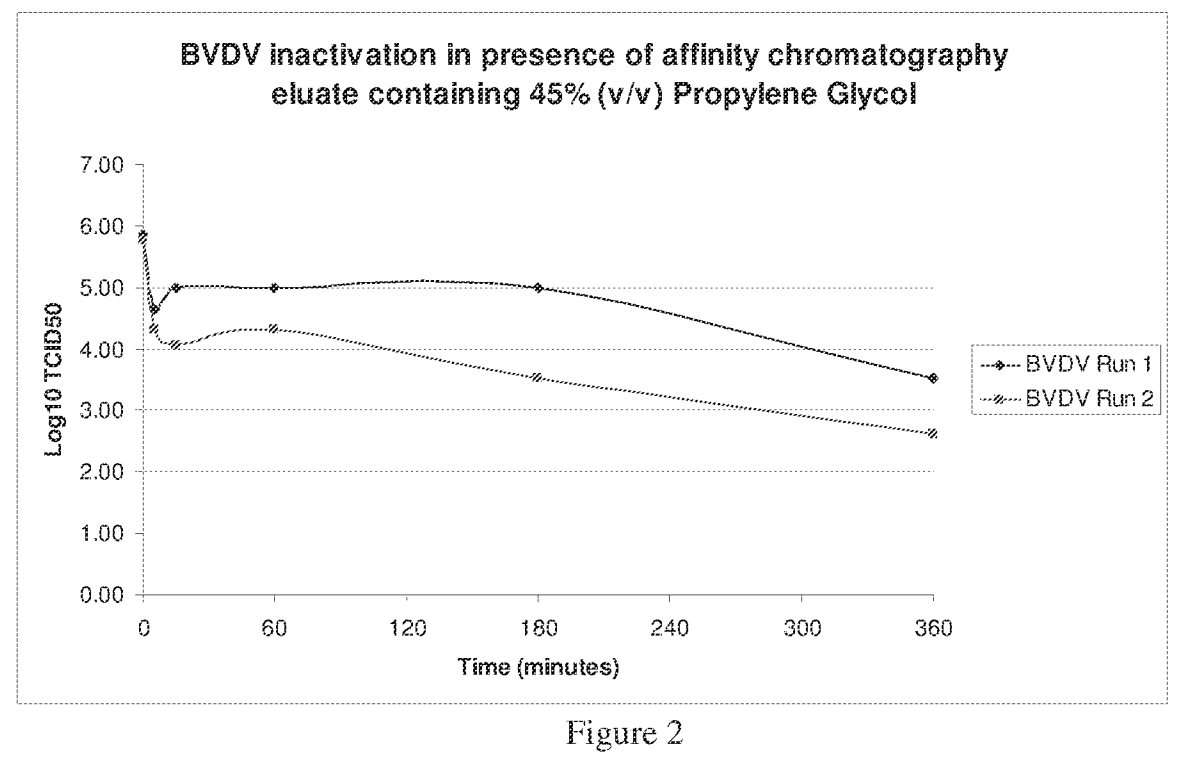

The results are described in Table IX and illustrated in FIG. 2.

TABLE IX

| Timepoint Sample | Volume (ml) | Titre ($\log_{10}TCID_{50}$/ml) | Correction (cytotoxicity) | Log10TICD50 | Reduction Factor (log) | Clearance Factor (log) | Titration |
|---|---|---|---|---|---|---|---|
| BVDV - Run 1 | | | | | | | |
| Spike | 1 | 6.28 | NA | 6.28 | NA | NA | Standard |
| T = 0 Load Sample | 20 | 3.12 | 27 | 5.85 | NA | 0.43 | Standard |
| T = 5 | 20 | 1.9 | 27 | 4.63 | 1.22 | 1.65 | Standard |
| T = 15 | 20 | 2.25 | 27 | 4.98 | 0.87 | 1.3 | Standard |
| T = 60 | 20 | 2.25 | 27 | 4.98 | 0.87 | 1.3 | Standard |
| T = 180 | 20 | 2.25 | 27 | 4.98 | 0.87 | 1.3 | Standard |
| T = 360 | 20 | 0.8 | 27 | 3.53 | >4.32 | 2.75 | Standard |
| BVDV - Run 2 | | | | | | | |
| Spike | 1 | 6.2 | NA | 6.20 | NA | NA | Standard |
| T = 0 Load Sample | 20 | 3.03 | 27 | 5.76 | NA | 0.44 | Standard |
| T = 5 | 20 | 1.59 | 27 | 4.32 | 1.44 | 1.88 | Standard |
| T = 15 | 20 | 1.32 | 27 | 4.05 | 1.71 | 2.15 | Standard |
| T = 60 | 20 | 1.59 | 27 | 4.32 | 1.44 | 1.88 | Standard |
| T = 180 | 20 | <0.8 | 27 | <3.53 | >2.23 | >2.67 | Standard |
| T = 360 | 20 | <-0.12 | 27 | <2.61 | >3.15 | >3.59 | 1 LVP |

X-MuLV and PRV Studies on the Affinity Chromatography Eluate (in Presence of 45% PG).

A similar study was done on a affinity chromatography eluted with 45% PG using the X-MuIV and PRV viruses and including the determination of standard deviations.

Results are described in Tables X and XI.

TABLE X

| | X-MuLV study. | | | |
|---|---|---|---|---|
| Sample | Titer (TCID50/ml) | Volume (ml) | Volume correction | Viral Load (log10) |
| Spiking Positive control | 8.03 ± 0.36 | — | — | — |
| Theoretical load (5% spike) | 6.71 ± 0.36 | 20 | — | 8.01 ± 0.36 |
| Control T = 0 h (w/o SD) | 4.80 ± 0.42 | 20 | 10 | 7.10 ± 0.42 |
| Control T = 6 h (w/o SD) | 0.59 ± 0.91 | 20 | 10 | 2.89 ± 0.91 |
| T = 0 h (+SD) | ≤0.78* | 20 | 100 | ≤4.08 |
| T = 1 h (+SD) | ≤0.78* | 20 | 100 | ≤4.08 |
| T = 3 h (+SD) | ≤0.78* | 20 | 100 | ≤4.08 |
| T = 6 h (+SD) (Standard titration) | ≤0.78* | 20 | 100 | ≤4.08 |
| T = 6 h (+SD) (LVP) | ≤-1.13* | 20 | 100 | ≤2.17 |
| T = 6 h (+SD) (LVP + ST) | ≤-1.13* | 20 | 100 | ≤2.17 |

TABLE XI

| | PRV study. | | | |
|---|---|---|---|---|
| Sample | Titer (TCID50/ml) | Volume (ml) | Volume correction | Viral Load (log10) |
| Spiking Positive control | 8.64 ± 0.32 | — | — | — |
| Theoretical load (5% spike) | 7.32 ± 0.32 | 20 | — | 8.62 ± 0.32 |
| Control T = 0 h (w/o SD) | 2.17 ± 0.30 | 20 | 10 | 4.47 ± 0.30 |
| Control T = 6 h (w/o SD) | ≤0.78* | 20 | 10 | ≤3.08 |
| T = 0 h (+SD) | ≤1.48* | 20 | 10 | ≤3.78 |
| T = 1 h (+SD) | ≤1.48* | 20 | 10 | ≤3.78 |
| T = 3 h (+SD) | ≤1.48* | 20 | 10 | ≤3.78 |
| T = 6 h (+SD) (Standard titration) | ≤1.48* | 20 | 10 | ≤3.78 |
| T = 6 h (+SD) (LVP) | ** | 20 | 10 | NA |

The foregoing written specification is considered to be sufficient to enable one skilled in the art to practice the invention. The present invention is not to be limited in scope by examples provided, since the examples are intended as a single illustration of one aspect of the invention and other functionally equivalent embodiments are within the scope of the invention. Various modifications of the invention in addition to those shown and described herein will become apparent to those skilled in the art from the foregoing description and fall within the scope of the appended claims.

The advantages and objects of the invention are not necessarily encompassed by each embodiment of the invention.

What is claimed is:

1. A method for inactivating and/or eliminating an enveloped virus for the production of a recombinant protein, said method comprising conducting affinity chromatography on a biological composition containing a recombinant protein, wherein the recombinant protein is eluted during the affinity chromatography with an elution buffer comprising propylene glycol, wherein the biological composition is a blood composition, a milk composition, urine, sweat, sputum, feces, spinal fluid, or cellular or tissue extracts, wherein the concentration of propylene glycol in the elution buffer is between 40 and 50% (v/v), and wherein the propylene glycol is not combined with arginine.

2. The method of claim 1, wherein said method is performed at a temperature between 15 and 25° C.

3. The method of claim 1, wherein said method is performed at a pH between 7.0 and 8.0.

4. The method of claim 1, wherein the affinity chromatography column is washed with a wash buffer prior to elution of the recombinant protein, wherein the concentration of propylene glycol in the wash buffer is between 30 and 40% (v/v).

5. The method of claim 1, wherein recombinant protein is maintained in the elution buffer with a concentration of propylene glycol between 40 and 50% (v/v) for less than 6 hours.

6. A method for inactivating and/or eliminating a virus during a purification of a protein from a biological composition, said method comprising contacting said biological composition during the purification of the protein with a glycol to inactivate the virus, wherein the concentration of glycol after the contacting step is between 40 and 50% (v/v) of the biological composition, and wherein the glycol is not combined with arginine.

7. The method of claim 6, wherein said glycol is propylene glycol.

8. The method of claim 6, wherein said biological composition is a blood composition or a milk composition.

9. The method of claim 6, wherein the virus is an enveloped virus.

10. The method of claim 6, wherein said method results in a viral elimination equal or greater than 4 $Log_{10}TCID$, wherein the TCID is according to the methods of Kärber and/or Spearman-Kärber.

11. The method of claim 6, wherein said method is performed at a temperature between 15 and 25° C.

12. The method of claim 6, wherein said method is performed at a pH between 7.0 and 8.0.

13. A method for inactivating a virus during the purification of a protein from a biological composition, said method comprising contacting an eluate with a glycol during the process of purification of the protein from the biological composition to inactivate and/or eliminate the virus, wherein the concentration of glycol after the contacting step is between 40 and 50% (v/v) of the elute, and wherein the glycol is not combined with arginine.

14. The method of claim 13, wherein said glycol is propylene glycol.

15. The method of claim 13, wherein said biological composition is a blood composition or a milk composition.

16. The method of claim 13, wherein the virus is an enveloped virus.

17. The method of claim 16, wherein said enveloped virus is selected from the group consisting of X-MuLV, PRV, BVDV and TGEV virus.

18. The method of claim 13, wherein said method results in a viral elimination equal or greater than 4 $Log_{10}TCID$, wherein the TCID is according to the methods of Kärber and/or Spearman-Kärber.

19. The method of claim 13, wherein said method is performed at a temperature between 15 and 25° C.

20. The method of claim 13, wherein said method is performed at a pH between 7.0 and 8.0.

* * * * *